(12) United States Patent
Grubbs et al.

(10) Patent No.: US 11,170,625 B2
(45) Date of Patent: Nov. 9, 2021

(54) HEAD POSITIONER FOR RETINAL SURGERY PATIENTS

(71) Applicants: CALIFORNIA INSTITUTE OF TECHNOLOGY, Pasadena, CA (US); THE REGENTS OF THE UNIVERSITY OF CALIFORNIA, Oakland, CA (US)

(72) Inventors: Robert H. Grubbs, South Pasadena, CA (US); Hyuck Choo, Yongin-si (KR); Frank L. Brodie, San Francisco, CA (US)

(73) Assignees: CALIFORNIA INSTITUTE OF TECHNOLOGY, Pasadena, CA (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 252 days.

(21) Appl. No.: 16/417,525

(22) Filed: May 20, 2019

(65) Prior Publication Data

US 2020/0051415 A1 Feb. 13, 2020

Related U.S. Application Data

(60) Provisional application No. 62/673,702, filed on May 18, 2018.

(51) Int. Cl.
*G08B 21/00* (2006.01)
*G08B 21/04* (2006.01)
(Continued)

(52) U.S. Cl.
CPC ........ *G08B 21/0446* (2013.01); *A61B 5/1116* (2013.01); *G01C 19/065* (2013.01); *G08B 25/10* (2013.01); *A61F 2009/0035* (2013.01)

(58) Field of Classification Search
CPC .. G08B 21/0446; G08B 25/10; G01C 19/065; A61B 5/116; A61B 5/6814; A61F 2009/0035; A61F 9/00727
See application file for complete search history.

(56) References Cited

U.S. PATENT DOCUMENTS

| 5,172,481 A | 12/1992 | Wiseman et al. |
| 5,645,077 A * | 7/1997 | Foxlin ............. A61B 5/1114 600/587 |

(Continued)

FOREIGN PATENT DOCUMENTS

EP 0740131 B1 5/2000

OTHER PUBLICATIONS

International Search Report and Written Opinion dated Jun. 1, 2016, corresponding to PCT/US2016/021068, 6 pages.

*Primary Examiner* — Ojiako K Nwugo
(74) *Attorney, Agent, or Firm* — Lewis Roca Rothgerber Christie LLP (57) ABSTRACT

A position sensing system comprises a position sensor having an accelerometer and a gyroscope, an alarm, and a controller configured to receive data from the position sensor and activate the alarm according to alarm management instructions stored in a memory. In some embodiments, the alarm instructions include a snooze option to allow the user/patient to temporarily deactivate the alarm. The controller is communicably linked to a remote display device configured to display the orientation of the user's body part.

19 Claims, 9 Drawing Sheets

(51) Int. Cl.
*G08B 25/10* (2006.01)
*G01C 19/06* (2006.01)
*A61B 5/11* (2006.01)
*A61F 9/00* (2006.01)

(56) References Cited

U.S. PATENT DOCUMENTS

| | | | |
|---|---|---|---|
| 6,032,375 A | 3/2000 | Shijo et al. | |
| 6,453,745 B1 | 9/2002 | Jalkanen | |
| 6,505,409 B2 | 1/2003 | Toda et al. | |
| 6,612,157 B2 | 9/2003 | Urano et al. | |
| 8,682,607 B2 | 3/2014 | Yamada et al. | |
| 8,725,436 B2 | 5/2014 | Yamada et al. | |
| 10,140,833 B1 * | 11/2018 | Jacobson | A61B 5/744 |
| 2004/0100357 A1 | 5/2004 | Kruse | |
| 2010/0201524 A1 * | 8/2010 | Gallagher | A61B 5/113 |
| | | | 340/573.1 |
| 2011/0313266 A1 | 12/2011 | Fortsch et al. | |
| 2012/0172681 A1 * | 7/2012 | Sun | A61B 5/1115 |
| | | | 600/301 |
| 2013/0060167 A1 * | 3/2013 | Dracup | G16H 50/20 |
| | | | 600/595 |
| 2014/0142485 A1 * | 5/2014 | Berry | A61B 5/1116 |
| | | | 602/19 |
| 2014/0276238 A1 * | 9/2014 | Osorio | A61B 5/16 |
| | | | 600/595 |
| 2015/0049002 A1 | 2/2015 | Ishikawa et al. | |
| 2015/0206410 A1 | 7/2015 | Yi et al. | |
| 2017/0312515 A1 * | 11/2017 | Ferree | A61B 5/4815 |
| 2018/0174420 A1 * | 6/2018 | Clark | G08B 25/10 |
| 2018/0228403 A1 * | 8/2018 | Li | A61B 5/7455 |
| 2019/0167095 A1 * | 6/2019 | Krueger | A61B 3/112 |

* cited by examiner

HEAD POSITIONER FOR RETINAL SURGERY PATIENTS

CROSS-REFERENCE TO RELATED APPLICATION(S)

This application claims priority to and the benefit of U.S. Provisional Application No. 62/673,702, filed May 18, 2018 and titled "HEAD POSITIONER FOR RETINAL SURGERY PATIENTS," the entire content of which is incorporated herein by reference.

BACKGROUND

Figure 1A:
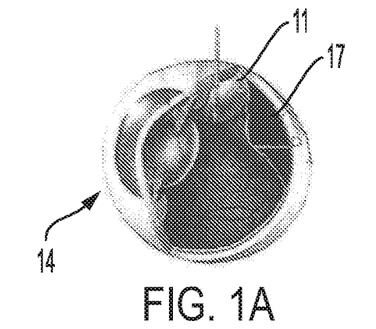
FIG. 1A is an illustration depicting an eye with a damaged retina undergoing pneumatic retinopexy.

Use of intravitreal tamponade with gas or silicone oil is an indispensable method to treat a number of retinal conditions, including rhegmatogenous retinal detachment and macular hole. In the case of retinal detachment, intravitreal gas or silicon oil is used to close and tamponade retinal breaks while a laser- or cryotherapy-induced chorioretinal adhesion forms around these breaks to prevent recurrent detachment. In the operating room, gas or silicone oil is used to fill the vitreous cavity at the time of vitrectomy; intravitreal gas to create a bubble 11 in a patient's eye 14, as shown in FIG. 1A, also can be injected in the office for selected cases of a torn or detached retina 17. Office/out-patient repair of retinal detachment with intraocular gas injection is called pneumatic retinopexy. Injection of intravitreal gas can also be used as an adjunct in the repair of retinal detachment using a scleral buckle, especially in the case of "fishmouthing" of retinal breaks overlying an encircling buckle.

Figure 1B:
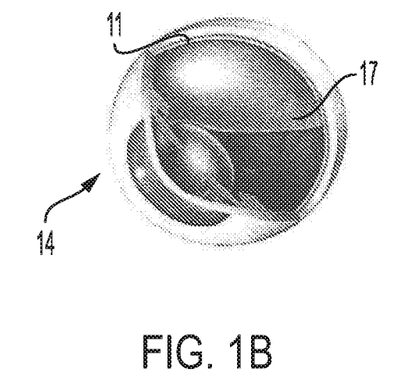
FIG. 1B is the illustration of FIG. 1A, clearly showing an intraocular bubble or silicone oil bubble at the 12 o'clock meridian.
Figure 2A:
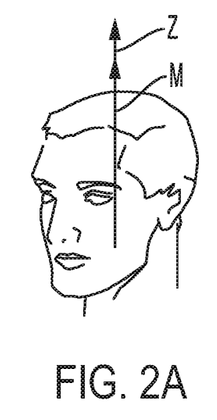
FIG. 2A is an illustration depicting a patient with an upright head position where a head meridian is generally vertically aligned with a Z axis.
Figure 2B:
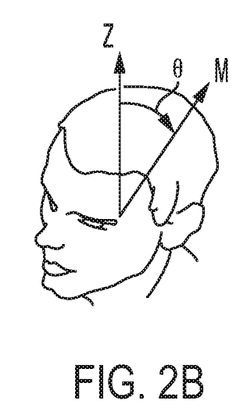
FIG. 2B is an illustration depicting the patient of FIG. 2A with a tilted head position, where the head meridian is at an angle relative to the Z axis.

In cases of retinal detachment repair using intraocular gas or silicone oil, the critical principle is to ensure the gas or silicone oil is in contact and completely covers the retinal detachment or break 17, as shown in FIG. 1B. The surface tension created between the oil or gas and the retinal break prevents vitreous fluid from passing through the break and re-accumulating underneath the retina (i.e. causing recurrent retinal detachment). Because both gas and silicone oil exert a flotation force in an aqueous environment, tamponade of a given retinal break requires that the break be positioned uppermost, as shown in FIG. 1B. For example, if a retinal break is located at the 12 o'clock meridian, then the bubble can be easily positioned over the retinal break with the patient situated in a normal sitting or standing position while holding his head in a vertical position (namely, wherein a longitudinal head meridian M is parallel with the Z axis, as shown in FIG. 2A). Alternatively, if the break is located at the 1:30 o'clock meridian, the patient's head must be tilted with an appropriate angle $\Theta$ maintained between the Z axis and the vertical head meridian M (as shown in FIG. 2B) to position the bubble over the break. If the head positioning is not correct and the appropriate angle $\Theta$ is not maintained as medically prescribed, the bubble may not cover ("close") the break, thus preventing retinal re-attachment.

Because it is often difficult for a patient to maintain proper head position (including the proper angle $\Theta$ or "tilt") to adequately tamponade a retinal break with intravitreal gas, incorrect head positioning can lead to failed retinal detachment surgery. Accurate control of head positioning can be difficult. Patients often cannot gauge the required tilt of their head to precisely position and/or precisely re-position a bubble over a retinal tear.

An often-used technique to assist the patient is to draw an arrow on an eye patch that is worn by the patient over the subject eye, with the arrow pointing to the meridian of the retinal tear. Then, the patient is instructed to tilt his/her head until the drawn arrow points to 12 o'clock, which effectively positions the bubble correctly relative to the retinal tear so that the flotation force can act on the retinal tear. This technique requires that patients continue to wear the eye patch (which most do not want to do) and frequently gaze in the mirror to confirm the arrow position. Additionally, this method does not help the patient maintain orientation during sleep.

Because of the difficulty of achieving and maintaining precise head positioning, it is not uncommon for patients to present with a persistent retinal detachment after uncomplicated pneumatic retinopexy. When asked to demonstrate the head position used since surgery, these patients frequently have not positioned properly, resulting in the bubble "missing" the retinal tear. If patients successfully position thereafter, the subretinal fluid resorbs, and the retina reattaches. If, however, the incorrect positioning has resulted in extension of the retinal detachment into the macula, the result can be permanent loss of central vision despite subsequent successful retinal reattachment.

Another clinical situation where intraocular gas is universally used is in the closure of macular holes. Following vitrectomy and removal of the internal limiting membrane, long-acting intravitreal gas is injected into the vitreous cavity and the patient is placed in a prone (face-down) position. Successful closure of a macular hole ordinarily requires seven days of strict face-down positioning. Inadequate positioning compliance causes persistent macular hole and resultant central vision loss.

Following successful closure of a macular hole with long-acting intravitreal gas, the bubble gradually resorbs over an additional period of one to eight weeks, depending on the type of gas injected. Patients are commonly instructed to maintain a face down position for one to seven days following the surgery. Additionally, patients need to avoid supine positioning that causes apposition between the bubble and the lens. Supine positioning, even if allowing only a few hours of contact between the bubble and the lens, can result in visually significant cataract formation.

As important as proper head positioning is with use of intraocular gas or silicone oil, patients are allowed to assume a more comfortable, neutral head position while eating or using the restroom. Normalization of head position for brief periods during the day appears to have no effect on anatomic and visual outcomes; the brief rests do make the rigors of proper head positioning less onerous.

Because use of prolonged intraocular tamponade is dependent on precise positioning while a bubble remains in the eye, improved methods to ensure proper head positioning are essential to optimize surgical and visual outcomes.

SUMMARY

According to some embodiments of the present disclosure, a device for ensuring proper head positioning is easy to use, can be portable and comfortably worn by the patient, and yet be effective in helping the patient maintain the proper head position.

In some embodiments, the device can be easily worn, removed and reworn by the patient without losing accuracy or precision of the proper head position. The device may also alert the patient when the patient's head position has deviated or changed from the proper head position.

In some embodiments, for example, a position sensing system includes a position sensor configured to couple to a body part, an alarm, and a controller. The position sensor includes a gyroscope and an accelerometer. The controller includes a storage and a processor. The storage includes alarm instructions, wireless communication instructions, and position sensing instructions. The processor is configured to process a signal from the position sensor according to the position sensing instructions to determine a measured orientation of the body part. The controller is configured to store in the storage, as orientation data, measurements of the measured orientation of the body part taken at regularly timed intervals, and the processor is configured to activate the alarm in response to the signal from the position sensor and the stored orientation data according to the alarm instructions.

According to some embodiments of the present disclosure, in order to process the orientation data, the processor may receive from the gyroscope measurements of angular velocity in terms of roll, pitch, and yaw at regularly timed intervals, and/or receive from the accelerometer measurements of acceleration compared to the constant gravitational force of the earth at regularly timed intervals, and calculate a measured orientation of the body part based on the measurements from the gyroscope and/or accelerometer.

In some embodiments of the present disclosure, the orientation data stored in the storage may include each of the measured orientations of the body part taken at a particular (or respective) time interval as determined by the processor according to the position sensing instructions, a calculation of the deviation of each of the measured orientations of the body part from a prescribed orientation of the body part, and a time (or time interval) at which each of the measured orientations of the body part was measured/recorded.

According to some embodiments of the present disclosure, the alarm instructions may instruct activation of the alarm when the calculated deviation of one of the measured orientations of the body part from the prescribed orientation exceeds a predetermined or threshold degree. The alarm instructions may also (or alternatively) instruct the processor to calculate, based on the times (or time intervals) at which each of the measured orientations of the body part were measured, a duration of time over which the measured orientation(s) of the body part deviated from the prescribed orientation of the body part by the threshold degree. And the alarm instructions may instruct activation of the alarm when the calculated duration of time over which the measured orientation(s) of the body part deviated from the prescribed orientation by the threshold degree exceeds a predetermined threshold duration of time. When the alarm is activated, the alarm serves to alert the user/patient that the body part is not in the correct orientation, and to prompt the user to re-orient or adjust the orientation of the body part to again comply with the prescribed orientation. In some embodiments, the alarm management instructions may allow for a "snooze" option in which the user/patient can temporarily turn off (or disable) the alarm without re-orienting or adjusting orientation of the body part. This "snooze" option allows the user/patient a limited amount of time to remain in a non-compliant orientation while completing certain tasks, e.g., eating, brushing teeth, etc.

In some embodiments of the present disclosure, the alarm may be an auditory, visual, or tactile alarm, or a combination thereof.

In some embodiments of the present disclosure, the controller may further include a wireless communication driver. The wireless communication driver may be configured to send and receive signals via a Wi-Fi, Bluetooth, or Bluetooth Low Energy connection, or a combination thereof.

In some embodiments of the present disclosure, the position sensor may be included in or on a head band. In some embodiments, the position sensor may be mounted on an adhesive (or have an adhesive backing) that is configured to couple the position sensor to the body part of the user.

In some embodiments of the present disclosure, a remote display device may communicate with the controller. The remote display device may include a display, a display memory, a display receiver configured to receive a signal from the controller, and a display processor configured to run display instructions contained in the memory in response to the signal received from the controller, thereby producing a graphical user interface on the display responsive to the signal received from the controller. In some embodiments of the present disclosure, the alarm instructions and position sensing instructions stored on the controller may be accessed and/or modified via the remote display device.

In some embodiments of the present disclosure the remote display device may be a mobile phone or other smart device, such as, for example, a wearable smart device (e.g., a smart watch or the like). In some embodiments, the remote display device may be a tablet computer.

In some embodiments of the present disclosure, the controller may communicate wirelessly with a remote server running a management application. In some embodiments, the remote display device may communicate wirelessly with a remote server running a management application.

In some embodiments of the present disclosure, the remote display device may store an application in the display memory that can be run by the display processor. The application may write the orientation data received from the controller (including the measured orientations of the body part taken at the regularly timed intervals) to a text file. The application may be additionally or alternatively configured to display the measured orientation of the body part of the user based upon the orientation data using the graphical user interface. Additionally or alternatively, the application may be configured to display textual or symbolic instructions to the user responsive to the signal received from the controller.

In some embodiments, a remote access device communicates with the remote server.

BRIEF DESCRIPTION OF THE DRAWINGS

These and other features and advantages of the present disclosure will be better understood by reference to the following detailed description when considered in conjunction with the accompanying drawings. It is understood that selected structures and features have not been shown in certain drawings so as to provide better viewing of the remaining structures and features.

DETAILED DESCRIPTION

Embodiments of the present disclosure feature a position sensing system (or apparatus) for sensing a change or deviation in the angle of tilt (or orientation) of a user's head (or other body part) from an original or prescribed angle (or original or prescribed orientation). For example, some embodiments of the present disclosure relate to sensing a change or deviation of the tilt of a user's head from a prescribed angle following a procedure such as pneumatic retinopexy where intravitreal gas or silicone oil is used as a tamponade. In some embodiments, real-time audiovisual feedback improves post-operative positioning of the user's head by increasing the ease of maintaining the prescribed tilt angle. An alarm feature may further alert the user if his/her head position has deviated from the prescribed tilt angle by too much and/or for too long a duration of time. In some embodiments, wireless communication between the components enables increased ease-of-use for both the user and/or physician.

Figure 3A:
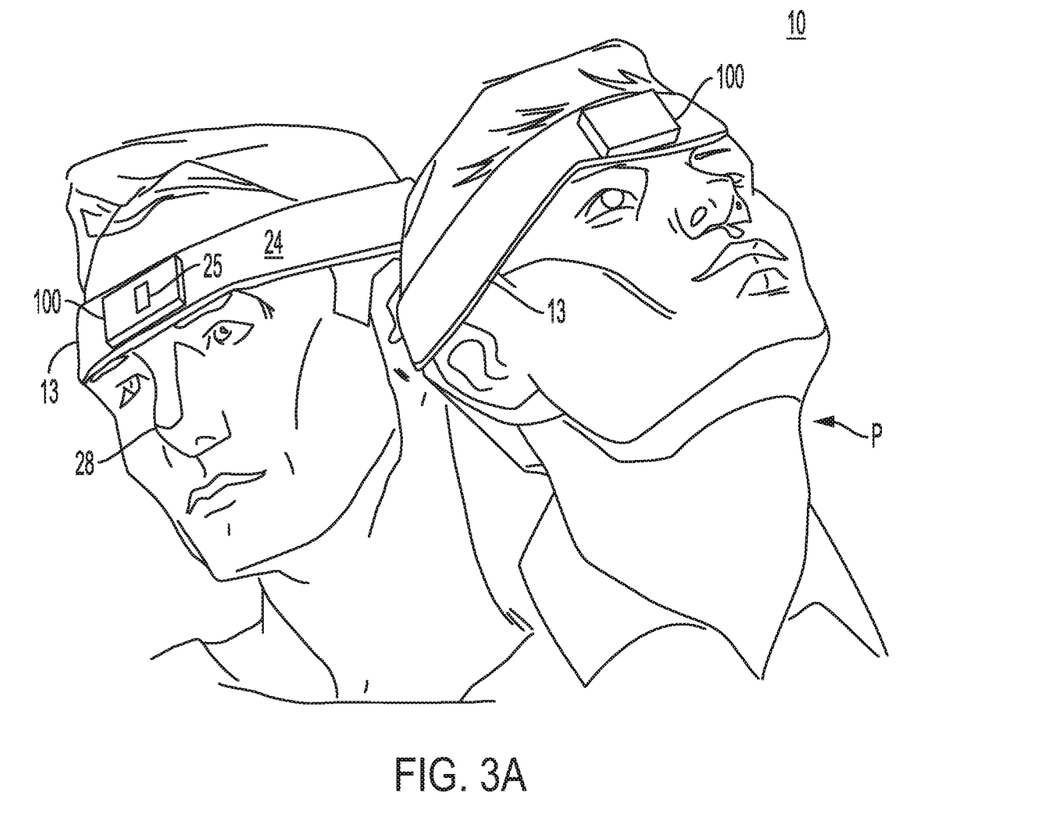
FIG. 3A is an illustration depicting a patient whose head is in different tilt angles while wearing a position sensor according to embodiments of the present disclosure.

According to some embodiments, a position sensing system (also referred to herein, interchangeably, as a position sensing apparatus) 100 is mounted on or in a mounting member 13. The mounting member 13 is not particularly limited, and may have any structure, shape or size sufficient to mount the position sensing system in an appropriate position on the body part of the patient/user (e.g., the head). As shown in FIG. 3A, for example, the mounting member 13 may include a headband. While FIG. 3A appears to depict the position sensing system 100 mounted on the headband, it is understood that the components of the position sensing system 100 (described further below) may alternatively be stitched in, or otherwise embedded or incorporated within the headband.

Figure 3B:
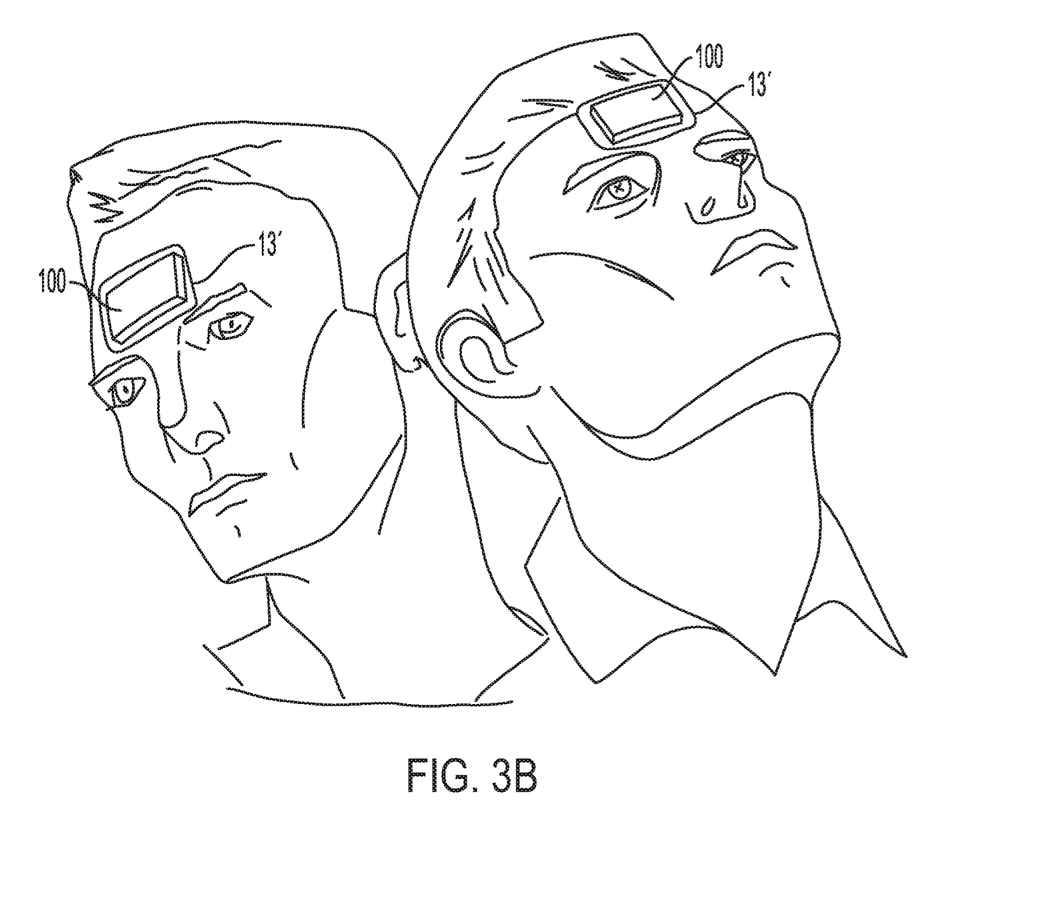
FIG. 3B is an illustration depicting a patient whose head is in different tilt angles while wearing a position sensor according to embodiments of the present disclosure.

Additionally, in some embodiments, the head band may encircle the circumference of the patient's head above the ears and thus be configured to be worn around the crown of the patient's head, as generally shown in FIGS. 3A and 3B. The head band may be flexible or semi-rigid, and adjustable to fit the patient's head. In these embodiments, the mounting member 13 (e.g., head band) has an outer surface 24 that is visible or exposed when the member 13 is worn on the patient's head. On the outer surface 24 may be one or more visual and/or tactile orientation indicia 25 that may be aligned with one or more features of the patient's head (or body), for example, the nose 28. As the position sensing system 100 may be embedded or stitched in the mounting member 13, these indicia 25 can be used to properly align the sensor on the patient's head. However, it is understood that when the position sensing system 100 is positioned on the mounting member 13 such that the system 100 is visible on the outer surface 24 of the mounting member 13, these indicia 25 may not be necessary, and therefore can be omitted.

In some embodiments, however, as shown generally in FIG. 3B, the mounting member 13' may include a simple adhesive backing on one side of the position sensing system 100. The adhesive backing 13' may be any suitable adhesive capable of adhering to the skin of the patient without damaging the skin. Suitable such adhesives are known to those of ordinary skill in the art. Additionally, the position sensing system 100 may be directly or indirectly embedded in or in contact with the adhesive of the adhesive backing. For example, when the position sensing system 100 is indirectly in contact with the adhesive, an intervening layer or sheet (such as, e.g., an intervening layer of paper, plastic or the like) may be between the position sensing system 100 and the adhesive. Also, the opposite side of the position sensing system 100 (i.e., the side opposite the adhesive) may be covered by top layer or sheet covering the position sensing system 100. The top layer or sheet is not particularly limited, and may be any suitable material including, e.g., paper, plastic or the like. In some embodiments, the top layer may be colored to match the skin of the patient, or simply be generally flesh colored to minimize the aesthetic intrusion of the device. However, in some embodiments, the top layer or sheet may be brightly colored or otherwise colored or patterned in order to draw attention to the device as a means to remind the user to comply with the prescribed tilt angle. Additionally, while the adhesive backing shown in FIG. 3A is depicted as extending beyond the perimeter of the position sensing system 100, the adhesive is not limited to such a construction. Instead, the adhesive may cover any portion of the side of the position sensing system 100, including a portion smaller than the total area of the system 100 or a portion equal to (but not exceeding) the total area of the system 100.

Figure 4:
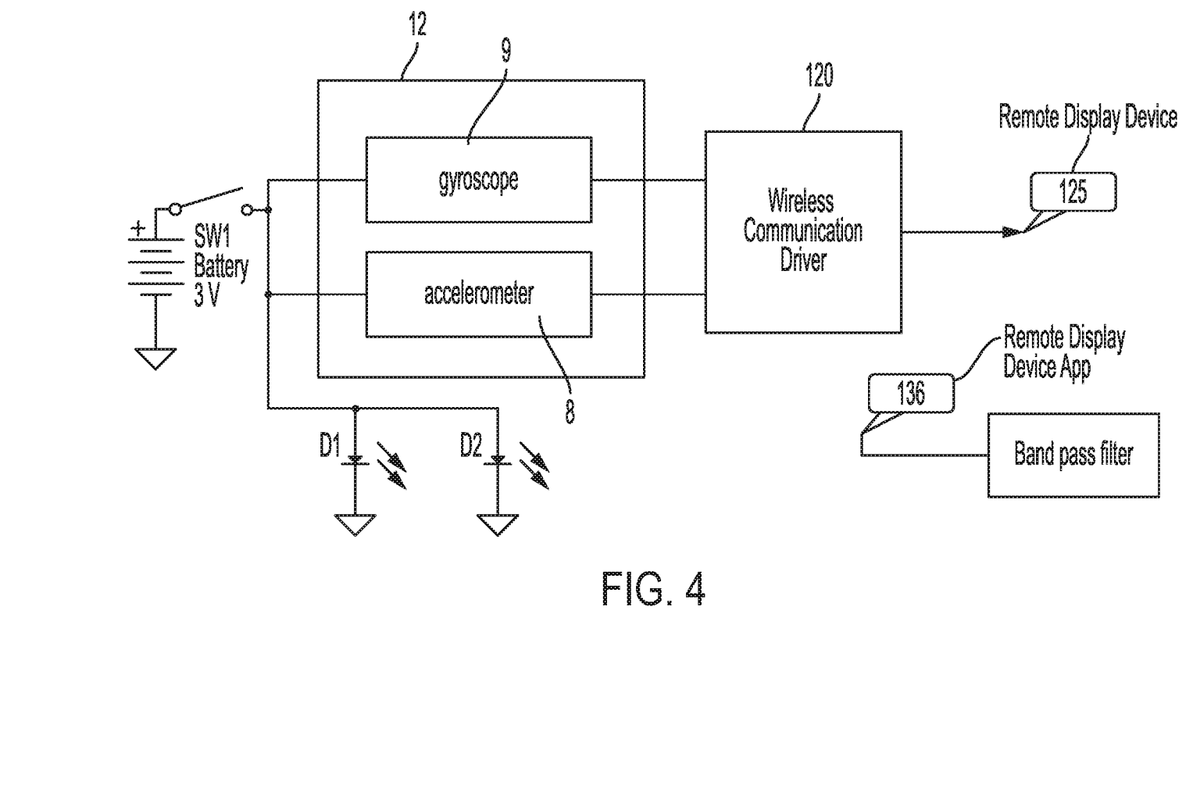
FIG. 4 is an illustration depicting a simplified circuit diagram of the position sensor and wireless communication driver in communication with a remote display device.

In some embodiments, the position sensing system 100 includes a position sensor 12 and other device components selected for communication and interaction with the position sensor 12 to accomplish certain goals or tasks (as discussed further below). As shown in FIG. 4, the position sensor 12 includes an accelerometer 8 and a gyroscope 9. The accelerometer 8 and gyroscope 9 may be linked to a power source (shown as Battery 3V in FIG. 4) and wired in parallel with one or more light emitting diodes (LEDs). The LEDs may be used to indicate when the device is powered on, and/or may be used to indicate when the position sensing system 100 is in an alarm state (as discussed further below).

According to some embodiments of the present disclosure, both the accelerometer 8 and the gyroscope 9 may be multi-axis devices. The accelerometer 8 may measure acceleration in the X, Y, and Z axes, and the gyroscope 9 may sense angular velocity in terms of roll, pitch, and yaw. The accelerometer values are compared to the constant gravitational force of the Earth. This provides for a stable calculation of the orientation angles.

Any suitable position sensor including an accelerometer and gyroscope may be used for these purposes, and suitable such sensors including accelerometers and gyroscopes are known to those of ordinary skill in the art. For example, in some embodiments, the position sensor may include the METAWEAR® line of wearable sensors (configured with the accelerometer/gyroscope option) available from Mbientlab Inc. (San Francisco, Calif.).

Figure 5:
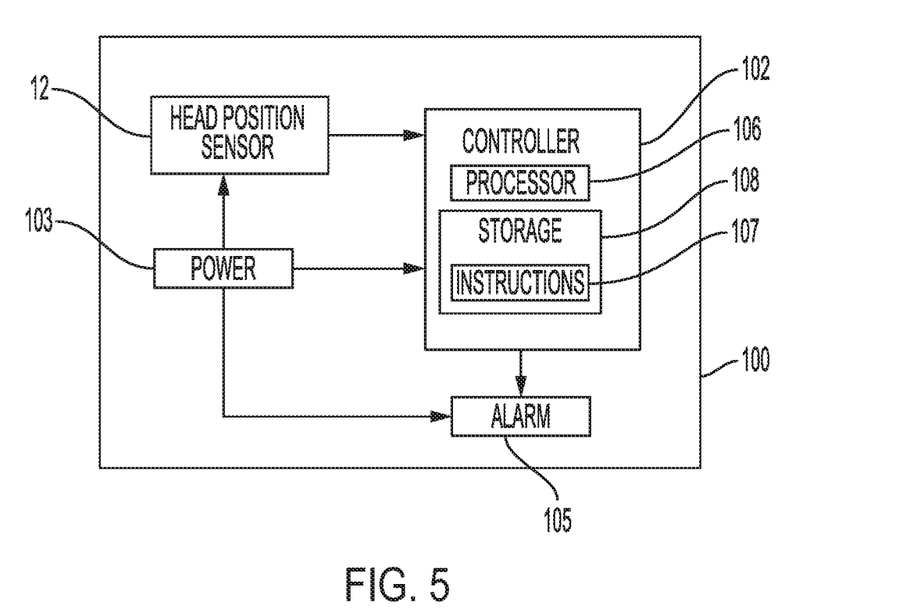
FIG. 5 is a block diagram of a position sensing apparatus, in accordance with embodiments of the present disclosure.

As noted above, the position sensing system 100 may include other device components in addition to the position sensor 12, which device components may be selected to communicate or otherwise interact with the position sensor 12 in certain ways to accomplish certain goals or tasks. For example, in some embodiments, the additional device components may include instructions, a storage, one or more processors, microelectronics, interfacing circuitry, etc. In some embodiments, the other device components include a controller 102, a power source 103, and an alarm 105, as shown in FIG. 5. Any suitable power source 103 may be used, and in some embodiments, the power source 103 may be AC- or DC-based (e.g., a battery).

In some embodiments, as shown in FIG. 5, the position sensing system 100 includes the position sensor 12 including the gyroscope 9 and accelerometer 8, and the alarm 105. The alarm 105 may be of any suitable form, for example, an auditory, visual or tactile alarm. The alarm 105 may be configured or programmed to activate (i.e., alert the user) upon the occurrence of a trigger event, such as, for example, when the user's body part has deviated from the prescribed orientation by more than a prescribed threshold degree (or value), and/or for more than a predetermined period of time. For example, in some embodiments, the alarm 105 may be configured to activate (i.e., place the system in an alarm state) when the system 100 determines that the user's body part (e.g., the head) has deviated from the prescribed orientation (or tilt angle) by more than a threshold (or predetermined) degree and remained in this deviated state (i.e., deviated by more than the threshold degree) for a threshold or (predetermined) amount of time. Configuring the alarm 105 in this manner allows the user enough leeway to move the body part for short periods of time without activating the alarm each and every time the body part deviates from the prescribed angle. Minimizing activation of the alarm in this manner to only more prolonged periods of noncompliance with the prescribed tilt angle will improve the likelihood that the user continues to wear the system/apparatus.

The alarm instructions may also be configured to include a "snooze" option in which the user/patient can temporarily deactivate the alarm. Such a snooze option deactivates the alarm for a short period of time to allow the user time to complete certain tasks that cannot be completed (or are difficult to complete) while the head (or other body part) is at the prescribed tilt angle (or orientation), such as, e.g., eating, changing clothes, etc. After selecting this option, the alarm will deactivate for a predetermined (or threshold) amount of time (i.e., the snooze duration), and after the snooze duration expires, the alarm will automatically reactivate to alert the user to reorient or adjust orientation of the body part back into compliance with prescribed tilt angle. The snooze duration may be any suitable amount of time, and may generally be selected to allow enough time for the user/patient to complete common tasks (such as, e.g., eating or changing clothes), but not long enough to jeopardize the treatment purpose. In some embodiments, for example, the snooze duration may be about 2 minutes to about 15 minutes, or about 2 minutes to about 10 minutes, and in some embodiments, about 5 minutes.

Also, in some embodiments, the snooze option may include more than one snooze duration for the user/patient to select when the system is in the alarm state. For example, when the system is in the alarm state, and the user/patient selects the snooze option, the alarm instructions may be configured to prompt the user/patient to select from different snooze durations, e.g., one option for 5 minutes, one option for 2 minutes and one option for 7 minutes. In some embodiments, this prompt may simply provide different durations of time (e.g., one option for 5 minutes, one option for 2 minutes and one option for 7 minutes) for the user/patient to select for the snooze duration. In other embodiments, the prompt may instead provide different tasks the user/patient is intending to complete over the snooze duration (e.g., one option for eating, one option for brushing teeth, one option for changing clothes, etc.). Each of the task options in these embodiments is pre-configured with a specified snooze duration, e.g., the eating option might be pre-configured to have a snooze duration of 10 minutes, while the brushing teeth option might be pre-configured to have a snooze duration of 3 minutes, and the changing clothes duration might be pre-configured to have a snooze duration of 5 minutes). Additionally, the alarm instructions may prompt the user to select an option from a list of options that includes both task options and simple time options, e.g., one option for eating, one option for 7 minutes, one option for brushing teeth, one option for 12 minutes, one option for changing clothes, one option for 15 minutes, etc. These embodiments provide the user/patient with flexibility in selecting the snooze duration based on the task the user/patient is trying to complete as well as the time it takes the user/patient to complete that task.

Additionally, in some embodiments, the alarm instructions may be configured to allow the user/patient to use the snooze option only once, or only a predetermined number of times (e.g., 1, 2 or 3 times). This ensures that the user/patient cannot "snooze" the alarm (and thus avoid reorienting the body part) for longer than a predetermined (or threshold) snooze duration set by the physician.

Figure 6:
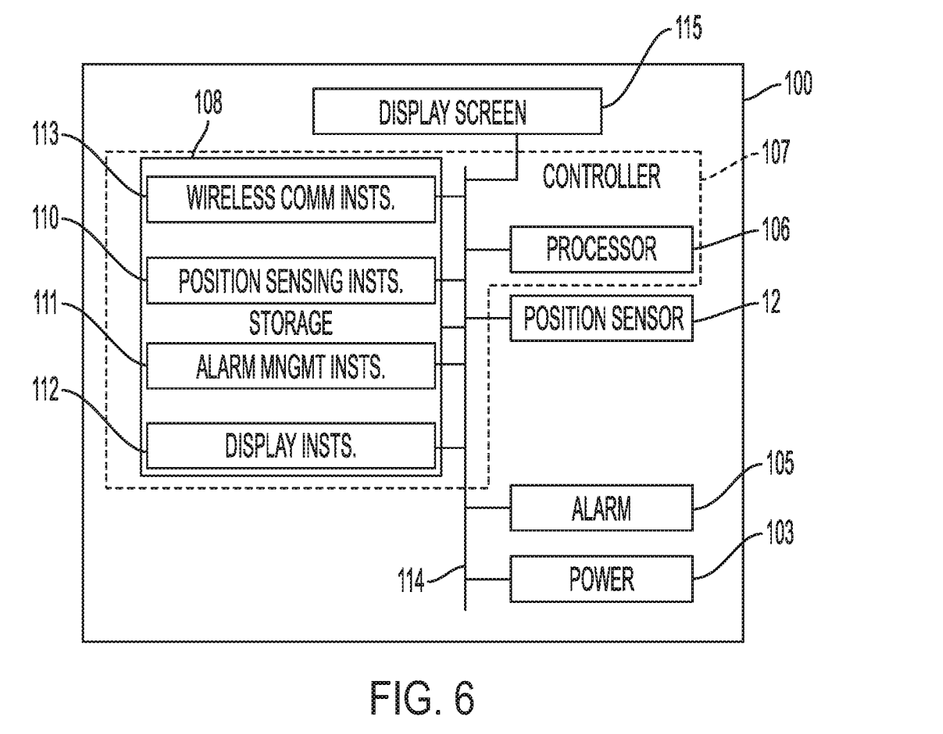
FIG. 6 is a block diagram of a position sensing apparatus, in accordance with embodiments of the present disclosure.

In some embodiments, as shown in FIGS. 5 and 6, the position sensing system 100 may further include a controller 102 having a storage 108, and a processor 106. In some embodiments, as shown in FIG. 7, the system 100 may also include a wireless communication driver 120.

Figure 7:
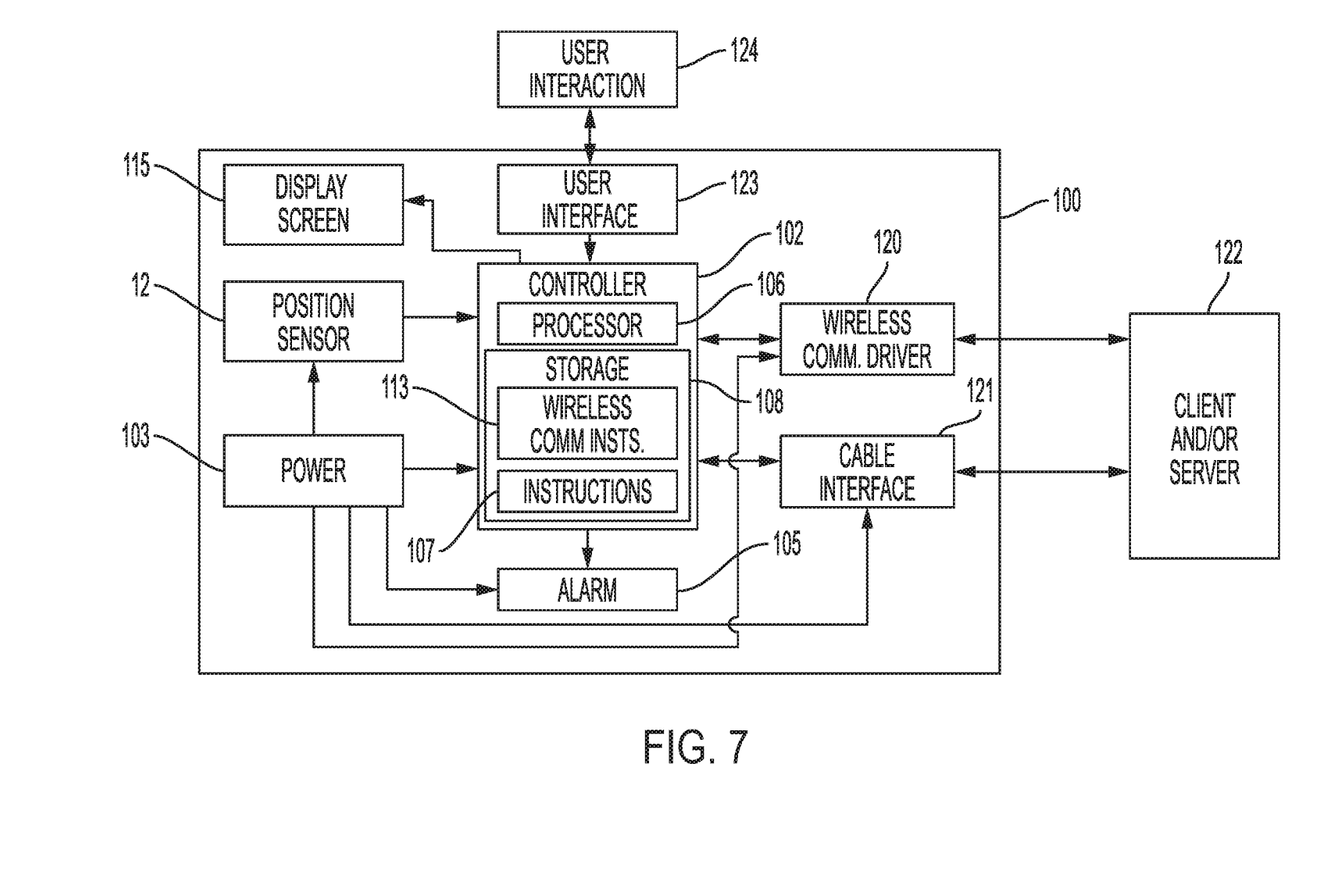
FIG. 7 is a block diagram of a position sensing apparatus, in accordance with embodiments of the present disclosure.

As noted above, in some embodiments, the controller 102 includes at least one processor 106, and a storage (e.g., a memory) 108 (with instructions 107), as shown in FIGS. 6 and 7. The instructions 107 may include position sensing instructions 110, alarm management instructions 111, display instructions 112, and/or wireless communication instructions 113 (FIGS. 6 & 7).

The processor 106 of the controller 102 functions in conjunction with the various instructions. In some embodiments, a single processor 106 can provide the functionality dictated by any one or all of the instructions. In other embodiments, multiple processors 106 (or chips) can be used to provide separate processing of any one of the instructions. As used here, "instructions" may refer to software, hardware, or any combination thereof. The storage 108 (and instructions 107), the processor 106, the sensor 12, the alarm 105 and the power source 103 can communicate with each other via a bus 114 (see FIG. 6). The storage 108 is in communication with the bus 114 for providing storage of the orientation data processed or tracked by the position sensing system 100. A battery or other power source 103 may be provided to power to the system.

The position sensing instructions 110 may be configured to, e.g., receive from the gyroscope 9 measurements of roll, pitch, and yaw at regularly timed intervals, receive from the accelerometer 8 measurements of acceleration in the X, Y, and Z axes at regularly timed intervals, and calculate a measured orientation of the body part and/or a duration for which the body part has maintained a specific orientation. This measured orientation and timing data is stored in the storage 108, and accessible by the other instructions (e.g., the alarm instructions 111, etc.) in the storage 108. As would be known to those skilled in the art, any suitable means of calculating a change in orientation using the data from the accelerometer 8 and/or the gyroscope 9 may be utilized. For example, the orientation can be calculated from the data produced by the gyroscope 9 and accelerometer 8 by using Riemann sums.

The alarm management instructions 111 include instructions that are configured to, e.g., activate the alarm when the measured orientation of the user's body part deviates from the prescribed orientation angle by more than a threshold amount $\Theta_T$, and/or when a prescribed time period for a treatment session has ended. Or, in some embodiments, the alarm management instructions 111 may be configured to activate the alarm (i.e., place the system 100 in the alarm state) when the system 100 determines that the user has deviated from the prescribed orientation angle by more than the threshold amount $\Theta_T$ for more than a predetermined or threshold period of time. By means of example, the alarm may be set to activate if the user's body part is more than 5-15 degrees (e.g., 8-12 degrees, or 10 degrees) off from the prescribed orientation for longer than about two minutes. In that regard, the alarm management instructions 111 may be configured to respond to data produced by the position sensing instructions 110.

The alarm management instructions 111 can also interface with a timekeeping module (e.g., clock, calendar, time zone, etc.) and can trigger activation of the alarm when certain conditions have been met (as discussed above). The alarm can be in the form of an audible alarm or a non-audible alarm provided on the mounting member 13 or elsewhere (e.g., the top sheet covering the system 100, or the remote display device, as discussed further below). The non-audible alarm can include a light or a vibration (or other tactile alarm). The light can be provided by a light source, and the vibration can be produced by a vibration motor.

In some embodiments, as depicted in FIG. 6, the position sensing system may further comprise wireless communication instructions 113. The wireless communication instructions 113 may be stored in the storage 108 and run by the processor 106. The wireless communication instructions 113 can be in the form of a circuit having radio communication capabilities. The radio communication capabilities can be in the form of a Wi-Fi connection, a Bluetooth connection, a low-energy Bluetooth connection, or any other form of wireless tethering or near field communication. The wireless communication instructions 113 are configured for communication of the position sensing system 100 with another computing device by way of a wireless signal. The wireless communication instructions 113 can interface with the controller for transferring orientation data, which may be stored in the storage 108, to the computing device.

In some embodiments, the system 100 further includes a display screen 115, as shown in FIG. 6 and FIG. 7, and display instructions 112 configured to instruct the system 100 to display information via the display screen 115. The display screen 115 can include, for example, liquid crystal display (LCD) screens, light emitting diode (LED) screens, organic light emitting diode (OLED) screens, plasma display screens, etc. The display screen 115 may be provided on a wearable device, for example, a device clippable to clothing or a wrist cuff. The wearable device may include the alarm 105, the display screen 115 and a button that can be pressed to activate the display screen 115, navigate to various metrics displayed on the screen, or to turn off the screen.

Figure 10A:
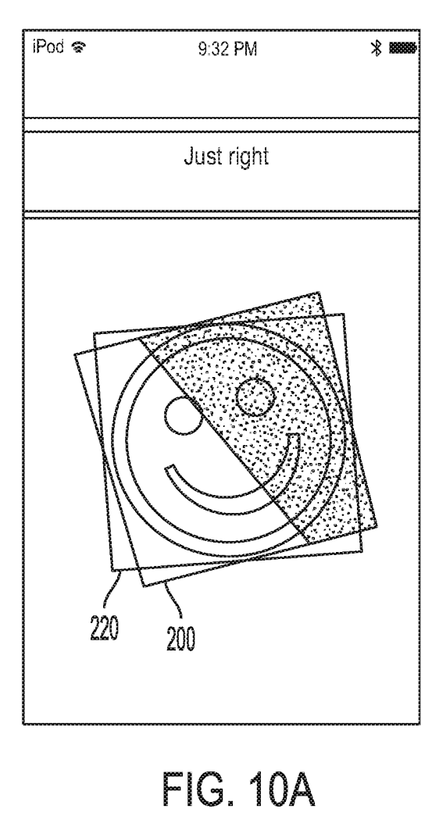
FIG. 10A is an illustration of an example pictorial representation on the remote display device indicating that the current measured orientation of the body part is within the tolerance allowed by the position sensing system, in accordance with embodiments of the present disclosure.
Figure 10B:
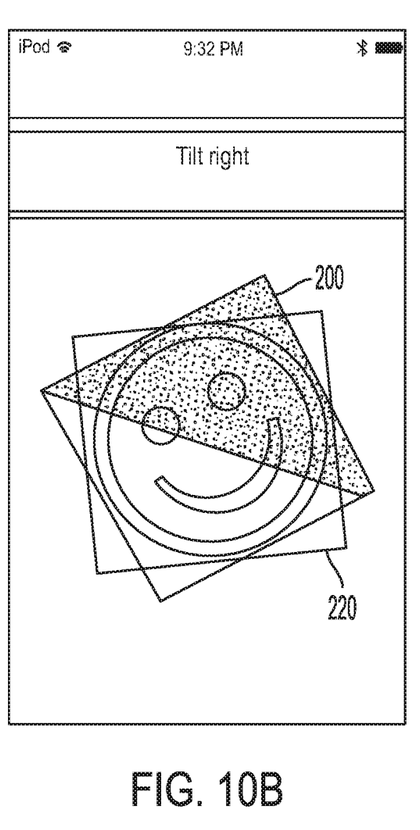
FIG. 10B is an illustration of an example pictorial representation on the remote display device indicating that the current measured orientation of the body part is outside the tolerance allowed by the position sensing system and providing instructions regarding how to bring the body part back into compliance, in accordance with embodiments of the present disclosure.

The information displayed on the screen is not particularly limited, and in some embodiments, may include simple text, e.g., instructing the user to adjust the tilt angle of the body part in a particular manner in response to the position sensing instructions 110 and/or alarm management instructions 111. In some embodiments, for example, the display instructions 112 may be configured to display on the display screen a pictorial representation of the current orientation of the user's body part (e.g., head) relative to the prescribed orientation. This pictorial representation is not particularly limited and may have any suitable format. In some embodiments, as shown in FIGS. 10A and 10B, for example, the pictorial representation may include a graphical representation of the current orientation of the user's body part (e.g., head) 200 superimposed on a still representation of the prescribed orientation 220. As can be seen in FIGS. 10A and 10B, such a pictorial representation graphically depicts whether the current orientation is within the tolerance allowed by the system (i.e., whether the current orientation deviates from the prescribed orientation by more or less than a threshold or predetermined degree, as discussed above). Additionally, because the pictorial representation depicted in FIGS. 10A and 10B depicts the real-time, actual orientation of the body part relative to the prescribed orientation, the pictorial representation also conveys to the user which way to tilt or adjust the body part to bring the current orientation back into compliance with the prescribed orientation. If desired, the display instructions 112 may also instruct the system to display text descriptions of the status of the current orientation or any needed adjustments (e.g., "Just right" as shown in FIG. 10A to indicate that any current deviation from the prescribed orientation is within the tolerance allowed by the system 100, or "Tilt right" as shown in FIG. 10B to indicate that the current orientation is outside the tolerance allowed by the system and to provide the user with instructions to correct the orientation). In the pictorial representations depicted in FIGS. 10A and 10B, the "smiley face" icon is representative of the body part, and that smiley face mirrors the current position of the body part as measured by the system 100. It is understood that the pictorial representations depicted in FIGS. 10A and 10B are illustrative examples only, and the pictorial representations according to embodiments of the present disclosure are not limited to these depictions. Indeed, any suitable pictorial representation may be used without limitation.

In some embodiments, as shown in FIGS. 4 and 7, the controller 102 may be configured to communicate using the wireless communication driver 120 with a remote display device 125. The remote display device 125 may be a computing device that is capable of communicating wirelessly with the system 100 and with the Internet 130. The remote display device 125 can support installation and execution of applications 126, which can be downloaded from a server 132. The server 132 may be a specialized server or a server that provides applications to devices, such as an application store. Once the application 126 is installed on the remote display device 125, the remote display device can communicate or be configured to communicate with the system 100. The remote display device 125 can be a smart phone or other smart device (such as, e.g., a wearable smart device, e.g., a smart watch), handheld computer, tablet computer, laptop computer, desktop computer, or any other computing device capable of wirelessly interfacing with the system 100 and the Internet 130.

The remote display device 125 may be configured to receive communications from the controller 102 responsive to the measured orientation of the user's body part. This communication can be in the form of a Wi-Fi connection, a Bluetooth connection, a low-energy Bluetooth connection, or any other form of wireless tethering or near field communication. The remote device 125 can also communicate with the Internet 130 using an Internet connection, which may include cellular communication, wireless connections (such as those described herein), and combinations thereof (such as connections to switches between different types of connection links).

As discussed generally above, communication and interaction with the remote display device 125 may be conducted using an application 126 stored on the remote display device 125. The application 126 may, in some embodiments, use Objective-C or another suitable programming language to store orientation data received from the controller in a text file. The application 126 may also display to the user via a graphical user interface the measured orientation of the body part relative to the prescribed orientation, such as the pictorial representation described above (and depicted in FIGS. 10A and 10B). Such a display may be produced using a Swift or other suitable programming language module. Written or symbolic instructions may be displayed within the application 126 to the user to guide them towards the prescribed orientation, as also described above. The application 126 may also provide alarm and display functions in lieu of or in addition to the alarm 105 and display screen 115.

The application 126 may further include instructions for a "tare" or calibration function. To use this function, the user assumes a neutral position (e.g., an un-tilted or straight orientation of the body part) and the position sensor data is "zeroed" or "tared" while the body part is in this neutral position, thereby allowing for accurate measurement of tilt angles following removal and replacement of the position sensing system 100 on the body part. As used herein, the terms "initial orientation," "reference orientation," "neutral orientation" and other like terms may be used interchangeably to refer to a position that can be easily reproduced by the user to allow for calibration of the sensor. These terms are not to be confused with the terms "measured orientation" (which refers to the orientation of the body part during a treatment session and relative to the prescribed orientation), and "prescribed orientation" (which refers to the orientation angle prescribed by the doctor, and identified the orientation the body part should be in during a treatment session). As a non-limiting example, such a reference or initial position of a head may be a normal upright position with the user facing forward to allow for the sensor to calibrate to that position as having zero tilt. This functionality provides ease of use, allowing the user to remove the position sensing system 100 for an activity like bathing or sleeping, and then replace the position sensing system 100 on the body part without a loss in accuracy when determining the orientation of the body part.

In some embodiments, the position sensing system 100 may further include a wireless communication driver 120, a cable interface 121, and a user interface 123, as shown in FIG. 7. According to some alternative embodiments, a cable interface 121 and a user interface 123 may be included within the remote display device 125. The user interface 123 may be configured to receive user interaction 124 that is in the form of physical contact (e.g., without limitation, tapping, sliding, rubbing, multiple taps, gestures, etc.). Alternately, or in addition, the user interface 123 may be configured to receive user interaction 124 that is in the form of nonphysical contact (e.g., without limitation, proximity sensors, button presses, touch sensitive screen inputs, graphical user interface inputs, voice inputs, sounds inputs, etc.). The position sensing system 100 can communicate with a client and/or server 122 using a cable connection, e.g., a USB port, or a wireless connection, which is enabled by wireless communication instructions 113 (see FIG. 7).

Figure 8:
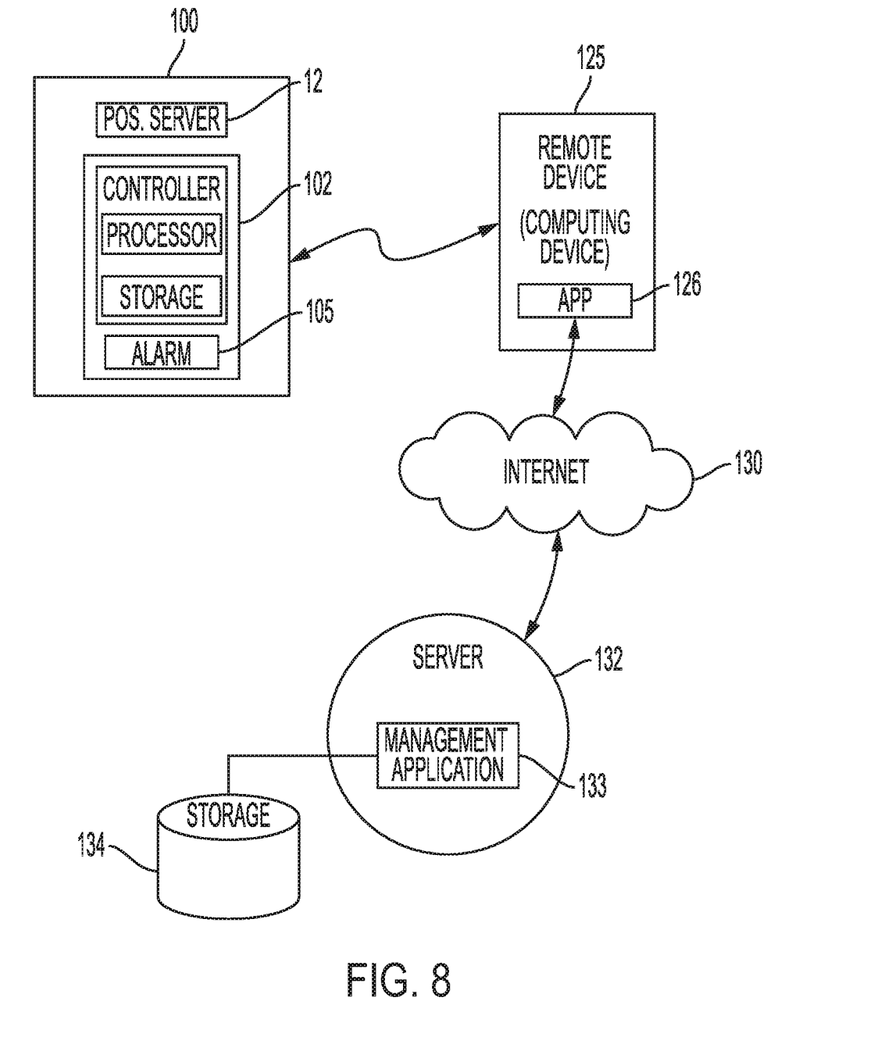
FIG. 8 is a block diagram of a position sensing apparatus in communication with a remote display device and a remote server, in accordance with embodiments of the present disclosure.

FIG. 8 illustrates an embodiment of the system 100 in communication with a remote display device 125. Remote display device 125 is a computing device that is capable of communicating wirelessly with the system 100 and with the Internet 130. Remote display device 125 can support installation and execution of applications. Such applications may include the application 126 of the present disclosure which can be downloaded from a server 132. The server 132 can be a specialized server or a server that provides applications to devices, such as an application store. Once the position sensing application 126 is installed in the remote display device 125, the remote display device 125 can communicate or be set to communicate with the position sensing system 100. The remote display device 125 can be a smart phone or other smart device (such as, for example, a wearable smart device, e.g., a smart watch or the like), a handheld computer, a tablet computer, a laptop computer, a desktop computer, or any other computing device capable of wirelessly interfacing with the system 100 and the Internet.

Figure 9:
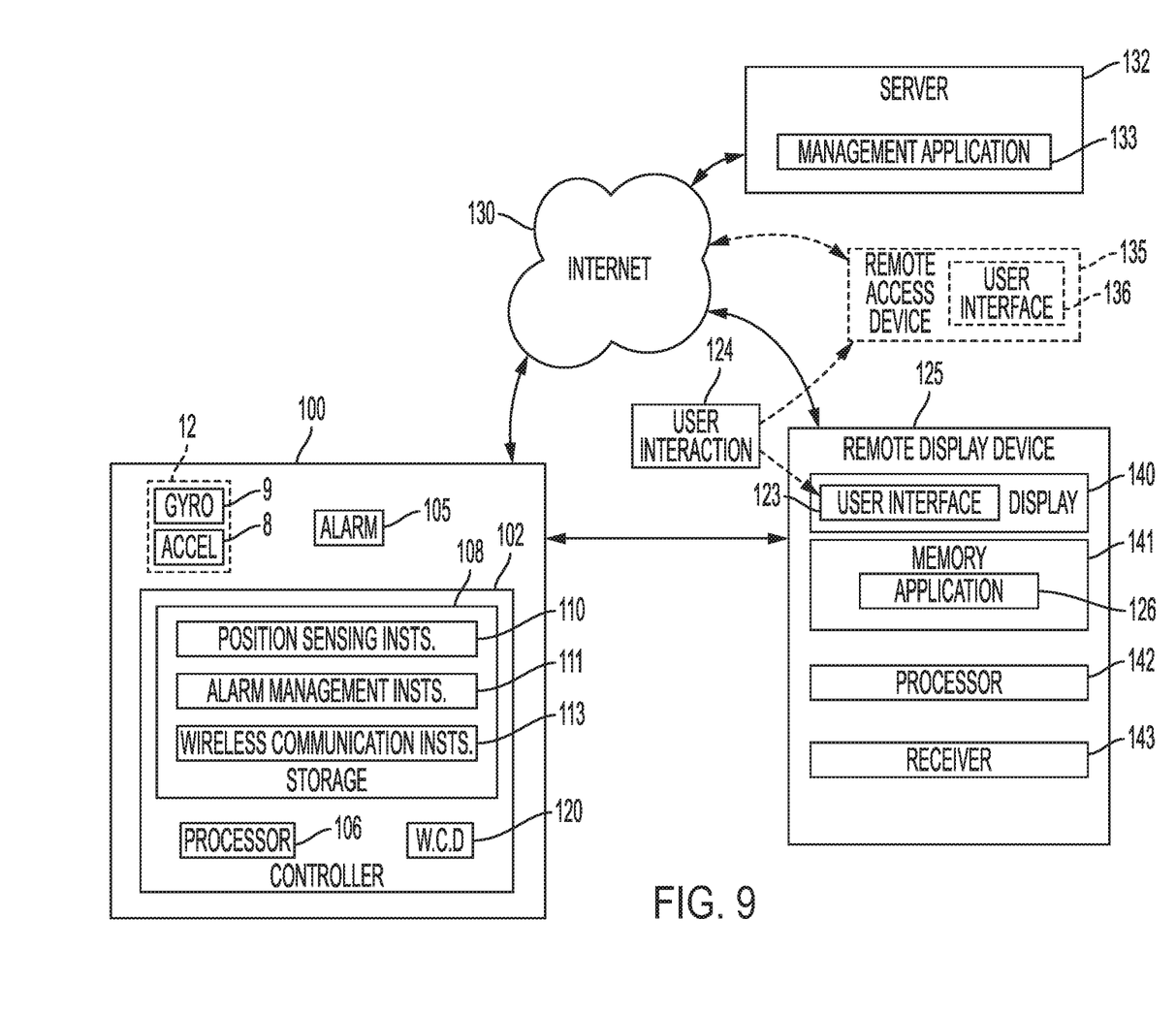
FIG. 9 is a block diagram of a position sensing apparatus in communication with a remote display device, a remote access device, and a remote server, in accordance with embodiments of the present disclosure.

As shown in FIG. 9, the remote display device 125 may include a display 140, a memory 141 containing an application 126, a processor 142, and a receiver 143. The display may include, for example, liquid crystal display (LCD) screens, light emitting diode (LED) screens, organic light emitting diode (OLED) screens, plasma display screens, etc. The display screen 140 may be provided on a wearable device, for example, a device clippable to clothing or a wrist cuff. The user interface 123 may be displayed on the display 140 and be configured to receive user interaction 124 that is in the form of physical contact (e.g., without limitation, tapping, sliding, rubbing, multiple taps, gestures, etc.). Alternately, or in addition, the user interface 123 may be configured to receive user interaction 124 that is in the form of nonphysical contact (e.g., without limitation, proximity sensors, button presses, touch sensitive screen inputs, graphical user interface inputs, voice inputs, sounds inputs, etc.). The receiver 143 is configured to allow for wireless communication between the system 100 and the remote display device 125. Furthermore, the receiver 143 can be configured, in some embodiments, to receive wireless communications via the Internet 130 from the remote server 132.

The server 132 may host a management application 133. The management application 133 may be configured to allow for various metrics derived from the orientation data collected by the controller 102 to be displayed to a user. The management application 133 may further comprise a user interface for displaying the various metrics via a website. Furthermore, the management application 133 may be configured to operate in conjunction with the remote display device 125 and/or a remote access device 135 to allow for control over the various instructions 107 stored on the storage 108 of the controller 102 via either the remote display device 125 (e.g., a patient's cell phone) or the remote access device 135 (e.g., a doctor's cell phone (or other smart device), tablet, computer, etc.) Allowing access to the instructions 107 via a remote access device allows the doctor to adjust tilt angles and tolerances of the position sensing system 100 remotely without the patient being present (such as, for example, if the patient forgets to bring his/her cell phone to a doctor's appointment).

Alternatively or additionally, these metrics may be shown in various graphical user interfaces on a website enabled by the server 132. As shown in FIG. 8, for example, enablement of the website can be through the implementation of a management application 133 run by the server 132. The website can include various pages with graphical user interfaces for rendering and displaying the various metrics for view by the patient or another user (e.g., the prescribing doctor). In some embodiments, the website can also include interfaces that allow for data entry and configuration by the patient or other user (e.g., the prescribing doctor).

Communication of the position sensing system 100 with the remote access device 135 according to some embodiments of the present disclosure is depicted in FIG. 9. As discussed above, the remote access device 135 may be configured to display metrics derived from the orientation data collected by the controller 102 and/or allow for control over the instructions 107 stored in the storage 108 of the controller 102. User interaction 124 may be conducted with the remote access device 135 via a user interface 136. It is understood that the user interface 123 of the remote display device 125 and the user interface 136 of the remote access device 135 may be different, as the data displayed by the devices to a user may be adjusted to suit different needs. For example, a physician accessing the orientation data of a patient via a remote access device 135 may view metrics based on the orientation data, such as, e.g., time within compliance. In contrast, a patient accessing the orientation data via a remote display device 125 may view real-time data (and/or pictorial representations) regarding the current orientation of his/her body part.

FIG. 9 additionally depicts embodiments of the disclosure in which the position sensing system 100 includes the position sensor 12 having the gyroscope 8 and accelerometer 9, an alarm 105, and a controller 102. As shown in FIG. 9, the controller 102 may include a storage 108 containing position sensing instructions 110, alarm management instructions 111, and wireless communication instructions 113. The controller may also include a processor 106 and a wireless communication driver 120. As shown in FIG. 9, the system 100 is in communication with the remote display device 125, which includes a display 140, a display memory 141 containing an application 126, a processor 142, and a receiver 143. The remote display device 125 may also include a user interface 123.

As also shown in FIG. 9, the position sensing system 100 may be in communication with the remote server 132 via a wireless communication link over the internet. As discussed generally above, the server 132 may include a management application 133. User interaction 124 with the system 100 may include interaction via a user interface 123 on the remote display device 125 or a user interface 136 of the remote access device 135.

As discussed in detail herein, embodiments of the present disclosure relate to a position sensor 12 configured to detect changes in the orientation or tilt angle of a patient's head (or other body part). For example, the position sensor 12 is part of a system that measures and calculates real-time deviations of a current body part orientation from a prescribed body part orientation. In some embodiments, for instance, after calibration of the system, and configuration of the position sensor 12 on the body part, the system 100 detects in real-time changes in the position of the patient's head (or other body part) that deviate from a prescribed tilt angle and guides the patient back to compliance with the prescribed angle using an alarm to alert the patient to deviations and visual instructions on which way to adjust the body part to bring it back into compliance.

In use, the position sensing system 100 is coupled to a user's body part using, for example, the mounting member 13 or adhesive 13' following a procedure such as pneumatic retinopexy. The position sensor 12 within the position sensing system 100 operates in conjunction with the controller 102 to allow for initial calibration of the position sensing system 100. This calibration may take place, for example, when the user has assumed a reference position and the position sensor 12 can be "zeroed" to an orientation in which the user's body part has no (or minimal or negligible) tilt angle. Once calibrated, the position sensing instructions 110 can be configured by setting a prescribed tilt angle. As discussed above, the position sensing instructions 110 will receive signals from the gyroscope and accelerometer of the position sensor 12 indicative of the current (or real-time) orientation of the body part and will calculate a deviation of the current orientation from the prescribed orientation (or prescribed tilt angle).

The physician may also program the alarm management instructions of the controller via the remote display device 125 or the remote access device 135 to activate the alarm based on one or more trigger events. For example, the physician may program the alarm instructions to activate the alarm whenever the current orientation deviates from the prescribed orientation by a threshold degree (e.g., 5-15 degrees, 8-12 degrees, or about 10 degrees). Additionally, in some embodiments, the physician may program the alarm instructions to activate the alarm only if the current orientation deviates from the prescribed orientation for longer than a threshold or predetermined amount of time (for example, about 1-3 minutes, or about 2 minutes). In some embodiments, for example, the physician may program the alarm instructions to activate the alarm only when the current orientation deviates from the prescribed orientation by more than the threshold degree and remains in that deviated state for longer than the threshold amount of time. Communication between the remote access device 135 or remote display device 125 and the position sensing system 100 may be conducted wirelessly over the Internet and be mediated by the remote server 132 running the management application 133.

While the system 100 is in use, the controller 102 processes signals from the position sensor 12 according to the position sensing instructions 110 contained in the storage 108. Orientation data stored in the storage 108 includes the current measured orientation, the deviation of the current measured orientation from the prescribed orientation, and the the time the measurement was taken (or the amount of time the measured orientation remaining in the deviated state). The processor 106 may access the storage 108 and process the orientation data in conjunction with the alarm management instructions 111 to determine if a triggering event has taken place necessitating activation of the alarm. As discussed above, such a triggering event may include deviation of the current measured orientation from the prescribed orientation by more than the threshold degree, and/or remaining in the deviated state for more than a threshold amount of time. Upon the occurrence of a triggering event, the controller 102 activates the alarm 105 (e.g., using the bus 114).

In addition to processing the orientation data according to the alarm management instructions 111, the processor 106 may also run the wireless communication instructions 113 to facilitate wireless communication of the orientation data with, e.g., a remote display device 125 or remote access device 135. This communication may take place using the wireless communication driver 120, which may broadcast the orientation data to the remote display device 125 or remote access device 135. The receiver 143 of the remote display device 125 (or remote access device) receives the signal from the wireless communication driver 120 and stores the orientation data in its memory.

The remote display device 125 (or remote access device) may utilize an application 126 to facilitate this process, for example, by having the application store the orientation data in a text file that is continuously updated. The application 126 may further utilize a module, such as a module programmed in Swift or another suitable programming language, to produce a graphical user interface in which the data from the text file is represented to the user. This may provide the user with real-time feedback regarding maintenance of the orientation of the body part within the threshold tolerance and instructions, for example, on what direction to move the body part to more closely align with the prescribed orientation. This instruction may be graphical in form (such as, for example, the pictorial representation described above), textual, or both graphical textual.

The wireless communication driver 120 may also communicate orientation data to the remote server 132 over the Internet 130. This facilitates additional storage redundancy for the orientation data, and allows for remote access to the data via the remote access device 135 (or remote display device 125). The remote server 132 may run the management application 133 to facilitate storage and analysis of the orientation data. The orientation data and various metrics derived from it may be made available to a user via a website or through a user interface on the remote access device 135. This functionality allows for a physician to monitor patient compliance and may further allow for control over the instructions 108 stored on the controller 102 via the remote access device 135. For example, a physician might extend the duration of time a patient may remain in a deviated state before the alarm will activate, may update the allowed tolerance (i.e., change the deviation degree allowed by the system before the alarm will activate), etc.

Although various embodiments of the disclosure have been described, additional modifications and variations will be apparent to those skilled in the art. For example, while the disclosed instructions and applications may be implemented via computer program instructions stored in memory and executed by a processor, the instructions and applications may also be implemented via hardware, firmware (e.g. ASIC), or any combination of hardware, firmware, and software as would be apparent to a person of ordinary skill in the art. As such, the disclosure is not limited to the embodiments specifically disclosed, and the systems, methods and sensors may be modified without departing from the disclosure, which is limited only by the appended claims and equivalents thereof.

Throughout the text and claims, any use of the word "about" reflects the penumbra of variation associated with measurement, significant figures, and interchangeability, all as understood by a person having ordinary skill in the art to which this disclosure pertains. Further, as used herein, the term "substantially" is used as a term of approximation and not as a term of degree, and is intended to account for normal variations and deviations in the measurement or assessment associated with the reported parameters.

What is claimed is:

1. A position sensing system, comprising:
a position sensor configured to couple to a body part, the position sensor comprising a gyroscope and an accelerometer;
an alarm;
a controller comprising:
a storage including alarm instructions, wireless communication instructions, and position sensing instructions; and
a processor configured to:
process a signal from the position sensor according to the position sensing instructions to determine a measured orientation of the body part at regular time intervals;
store in the storage, as orientation data, the measured orientation of the body part at the regularly timed intervals; and
activate the alarm in response to the stored orientation data according to the alarm instructions; and
a remote display device in communication with the controller, the remote display device comprising:
a display;
a display memory;
a receiver configured to receive a signal from the controller; and
a display processor configured to run instructions contained in the display memory in response to the signal received from the controller, thereby producing a graphical user interface on the display responsive to the signal received from the controller,
the remote display device being configured to store an application in the display memory that can be run by the display processor, and the application being configured to either:
display a pictorial representation of the measured orientation of the body part relative to a prescribed orientation, or
display textual or symbolic instructions to the user to guide the user to reorient the body part closer to the prescribed orientation.

2. The position sensing system according to claim 1, wherein to determine the measured orientation of the body part at the regular time intervals, the processor is configured to:
receive from the gyroscope measurements of angular velocity in terms of roll, pitch, and yaw at the regularly timed intervals;
receive from the accelerometer measurements of acceleration compared to the constant gravitational force of the earth at the regularly timed intervals; and
calculate the measured orientation of the body part based on the measurements from the gyroscope and/or accelerometer.

3. The position sensing system according to claim 2, wherein the orientation data comprises:
the measured orientation of the body part at the regularly timed intervals;
measurement of a deviation of the measured orientation of the body part at each of the regularly timed intervals from the prescribed orientation of the body part; and
a time at which each of the measured orientations of the body part was calculated.

4. The position sensing system according to claim 3, wherein the alarm instructions comprise:
- determining if each of the measurements of the deviation of the measured orientation of the body part from the prescribed orientation of the body part exceeds a threshold degree;
- calculate, based on the times at which each of the measured orientation of the body part was calculated, a duration of time over which each of the measurements of the deviation of the measured orientation of the body part from the prescribed orientation of the body part exceeds the threshold degree; and
- activate the alarm if the duration of time exceeds a threshold duration of time.

5. The position sensing system according to claim 1, wherein the alarm is an auditory, visual, or tactile alarm, or a combination thereof.

6. The position sensing system according to claim 1, wherein the controller further comprises a wireless communication driver.

7. The position sensing system according to claim 6, wherein the wireless communication driver is configured to send and receive signals via a Wi-Fi, Bluetooth, or Bluetooth Low Energy connection, or a combination thereof.

8. The position sensing system according to claim 1, further comprising a head band, wherein the position sensor is mounted on the head band, or stitched within the head band.

9. The position sensing system according to claim 1, further comprising an adhesive configured to couple the position sensor to the body part of the user.

10. The position sensing system according to claim 1, wherein the alarm instructions are configured to provide a snooze option to allow temporary deactivation of the alarm by the user without adjusting orientation of the body part.

11. The position sensing system according to claim 1, wherein the remote display device has remote access to the alarm instructions and position sensing instructions stored on the controller.

12. The position sensing system according to claim 1, wherein the remote display device is a mobile phone or a wearable smart device.

13. The position sensing system according to claim 1, wherein the remote display device is a tablet computer.

14. The position sensing system according to claim 1, wherein the controller is configured to communicate wirelessly with a remote server running a management application.

15. The position sensing system according to claim 1, wherein the remote display device is configured to communicate wirelessly with a remote server running a management application.

16. The position sensing system according to claim 15, further comprising a remote access device in communication with the remote server.

17. The position sensing system according to claim 1, wherein the application is configured to write the orientation data received from the controller to a text file.

18. The position sensing system according to claim 17, wherein the application is configured to display the pictorial representation of the measured orientation of the body part relative to the prescribed orientation.

19. The position sensing system according to claim 17, wherein the application is configured to display the textual or symbolic instructions to the user to guide the user to reorient the body part closer to the prescribed orientation.

* * * * *